Figure 1:
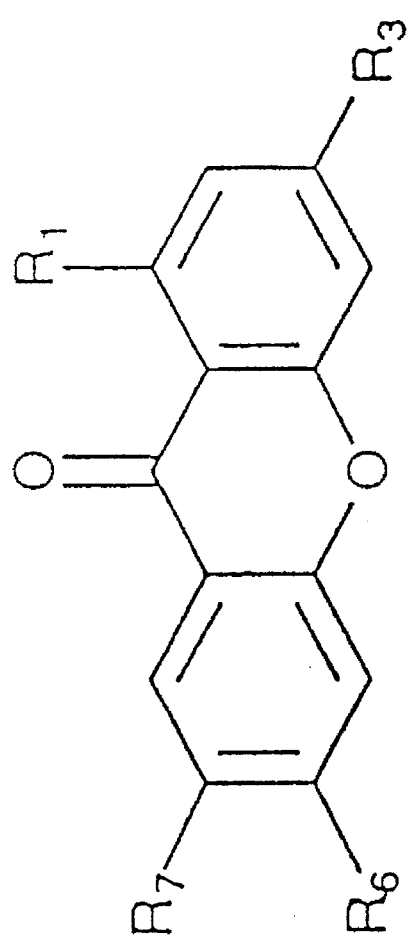

United States Patent

Lin et al.

Patent Number: 5,495,005
Date of Patent: Feb. 27, 1996

[54] SYNTHESIS AND PHARMACOLOGICAL ACTIVITY OF A SERIES OF NOVEL XANTHONE DERIVATIVES

[75] Inventors: Chun-Nan Lin, Tainan; Che-Ming Teng, Taipei; Ing-Jun Chen, Kaohsiung; Shwu-Jen Liou, Yun-Lin; Shorong-Shii Liou, Nan-Tou; Feng-Nien Ko, Taipei, all of Taiwan

[73] Assignee: National Science Council, Taipei, Taiwan

[21] Appl. No.: 112,704

[22] Filed: Aug. 26, 1993

[51] Int. Cl.$^6$ .................................. C07H 15/244
[52] U.S. Cl. ................... 536/18.1; 544/150; 546/196; 549/392
[58] Field of Search ............... 544/150; 546/196; 549/392; 514/455, 821, 869; 536/18.1

[56] References Cited

U.S. PATENT DOCUMENTS

| | | | |
|---|---|---|---|
| 3,532,711 | 10/1970 | Archer | 260/326.5 |
| 3,555,043 | 1/1971 | Archer | 260/328 |
| 3,912,733 | 10/1975 | Santilli et al. | 260/247.5 |
| 3,988,335 | 10/1976 | Santilli et al. | 260/247.5 |
| 4,816,479 | 3/1989 | Koga et al. | 514/455 |

FOREIGN PATENT DOCUMENTS

| | | |
|---|---|---|
| 04368379 | 12/1992 | Japan. |
| 05170969 | 7/1993 | Japan. |
| 9309470 | 5/1993 | WIPO. |

OTHER PUBLICATIONS

Teng et al. *Biochem. Pharmacol.*, 38(21), pp. 3791–3795, (1989). *(see p. 22).
Lin et al. *Shoyakugaku Zasshi*, 38(2), pp. 155–158, (1984). *(see p. 22).
Lin et al. *Phytochemistry*, 21(4), pp. 948–949, (1982). *(see p. 23).
Holloway et al. *Phytochemistry*, 14(11), pp. 2517–2518, (1975). *(see p. 28).
Litvinov et al. *Izv. Akad. Nauk, Ser. Khim.*, (2), pp. 329–335, (1992). *(see p. 6).
Bhavsar et al. *Man Made Text. India*, 32(5), pp. 183–194, (1989). *(see p. 20).
Liang et al. *Yaoxue Xuebao* vol. 17(8), pp. 587–591, (1982).
Aurell et al. *Journal of Nautral Products* vol. 52(4), pp. 852–857, (1989).
Lin et al. *J. Pharm. Sci* vol. 81(11), pp. 1109–1112, (1992).
Lin et al. *J. Pharm. Sci* vol. 81(1), pp. 11–16, (1993).
Chen et al. *Gen Pharmac.* vol. 24(6), pp. 1425–1433, (1993).

*Primary Examiner*—Douglas W. Robinson
*Assistant Examiner*—Howard C. Lee
*Attorney, Agent, or Firm*—W. Wayne Lianh

[57] ABSTRACT

A compound, and salts thereof, represented by either formula I or formula II below:

(1) Formula I:

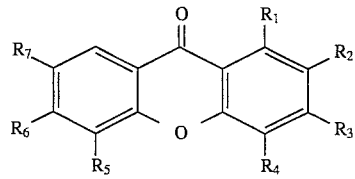

wherein substituents $R_1$–$R_7$ can be, independently, hydrogen, hydroxy group, $C_{1-6}$ alkyl(oxy) group, acetyl ester, or $C_{1-12}$ alkyl propanolamine; at least three but no more than four of the substituents are alkyl(oxy) group, hydroxyl group or acetyl ester; no more than one of the substituents can be $C_{1-12}$ alkyl propanolamines; $R_1$, $R_3$, $R_7$ cnnnot all be hydroxy groups at the same time; and $R_6$ is either an hydroxy group or an oxygen-containing glucose.

(2) Formula II:

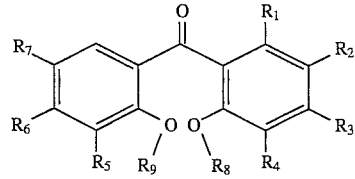

wherein substituents $R_1$–$R_9$ can be, indenpendently, hydrogen, hydroxy group and $C_{1-6}$ alkyl(oxy) group; and no more then four of the substituents can be methoxy group, hydroxy group, or acetyl ester. These compounds were tested to be capable of inhibiting platelet aggregation, atrioventricular conduction, and calcium influx in myocardial cells.

1 Claim, 12 Drawing Sheets tripteroside  $R_1 = R_3 = R_7$   $R_6 = O\text{-}Glu$ norathyrol  $R_1 = R_3 = R_6 = R_7$

SYNTHESIS AND PHARMACOLOGICAL ACTIVITY OF A SERIES OF NOVEL XANTHONE DERIVATIVES

DESCRIPTION OF THE DISCLOSURE

Hypertension has been one of the leading factors for the high death rate. The causes for hypertension is not only closely related to the cardiovascular and cerebral problems but also determined by others such as kidney diseases and diabetes. Currently, blood pressure-lowering drugs are available to prevent hypertension and consequently hinder the occurrence of stroke and heart-failure. However, these agents cannot prevent or cure coronary artery disease (CAD). Consequently, the development of an anti-hypertensive drug, which is safe, has little side-effect, and can prevent or cure the CAD, is highly demanded.

The reasons for CAD are plenty. If the abnormality of coronary artery results from thrombus formation and blood vessel constriction due to local platelet aggregation, then a drug has to be capable of both inhibiting the platelet aggregation and lowering the blood pressure in order to treat the patients with CAD. This type of drug is specifically called an antithrombotic-antihypertensive agent.

In addition to the local aggregation of platelet, the abnormality and constriction of blood vessels are also believed to enhance the formation of thrombus. The abnormalities could arise from either the elevated level of plasma cholesterol and triglyceride or damage to the lining endothelium due to other factors. Usually the latter, the damage to the lining endothelium, is a physiologically normal reaction because the endothelium is not only a protective layer of the blood vessel, but it also releases the prostacyclin ($PGI_2$) and endothelium-derived releasing factor (EDRF) that dilates the blood vessel and subsequently increase the blood flow. At present, some so called $Ca^{+2}$ channel blockers like nifedipine and verapamil are commercially available. These drugs can inhibit the calcium influx and consequently relieve the constriction of the blood vessels However there is no drug available which can prevent damage to the lining endothelium or trigger the release of $PGI_2$ and EDRF.

If CAD results from blood vascular constriction or the thrombus formation which results in a clog or a shortage of blood supply to the heart muscle and reduces the efficacy of the heart, then the patient will show the syndrome of arrhythmia. There are drugs on the market to inhibit arrhythmia. Nevertheless their severe side effects limit their clinical application. Since it can not only dilate blood vessels but also inhibit arrhythmia, this invention, the synthesized antithrombotic-antihypertensive agent with low toxicity, should be ideal to treat the patients with heart and vascular diseases.

As published on *Biochem. Pharmacol* (1989) 38:3791 Teng, and coworkers found that the xanthone derivatives (as shown in FIG. 1), isolated from Formosan Tripterospermum plants, tripteroside acetate and norathyrol acetate showed strong inhibition on platelet aggregation. Ko and coworkers (*European J. Pharmacol.* (1991) 192:133) reported that norathyriol, could strongly relax the peripheral blood vessels, significantly depress the atrioventricular conduction of a rabbit and also inhibit the calcium influx in myocardiac cells.

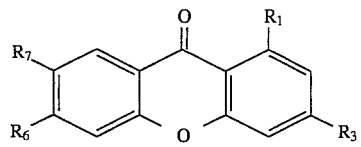

Figure 1. tripteroside $R_1 = R_3 = R_7$    $R_6 =$ O-Glu
norathyrol $R_1 = R_3 = R_6 = R_7$

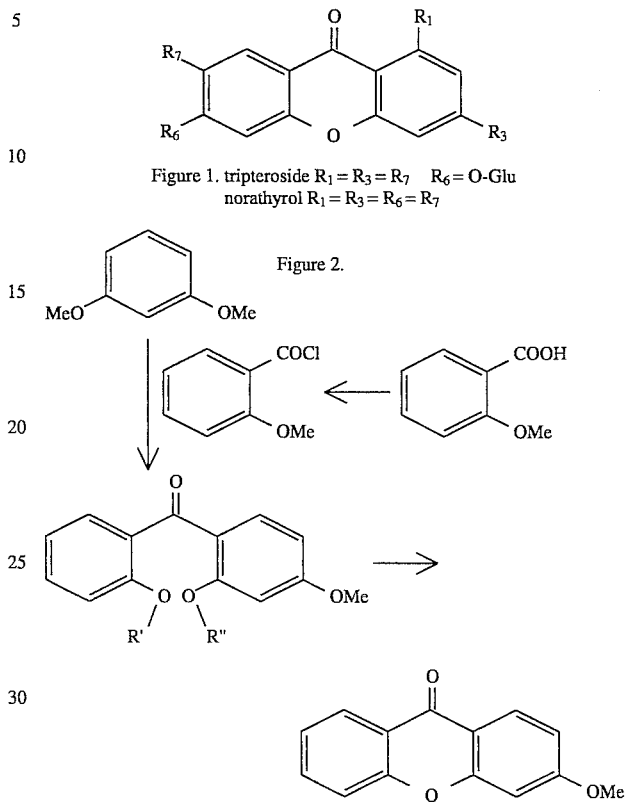

Figure 2.

Figure 2:
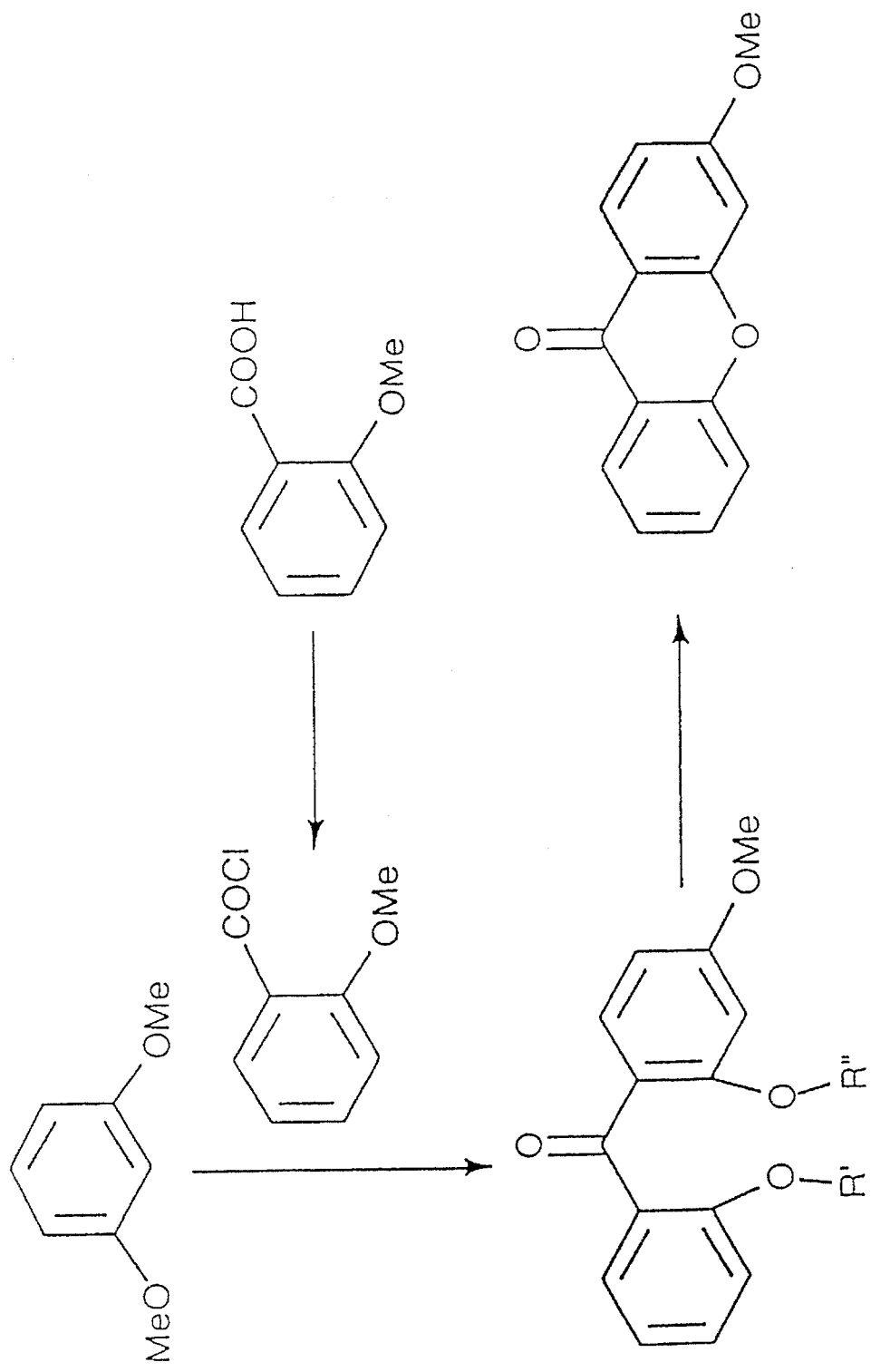
Figure 3:
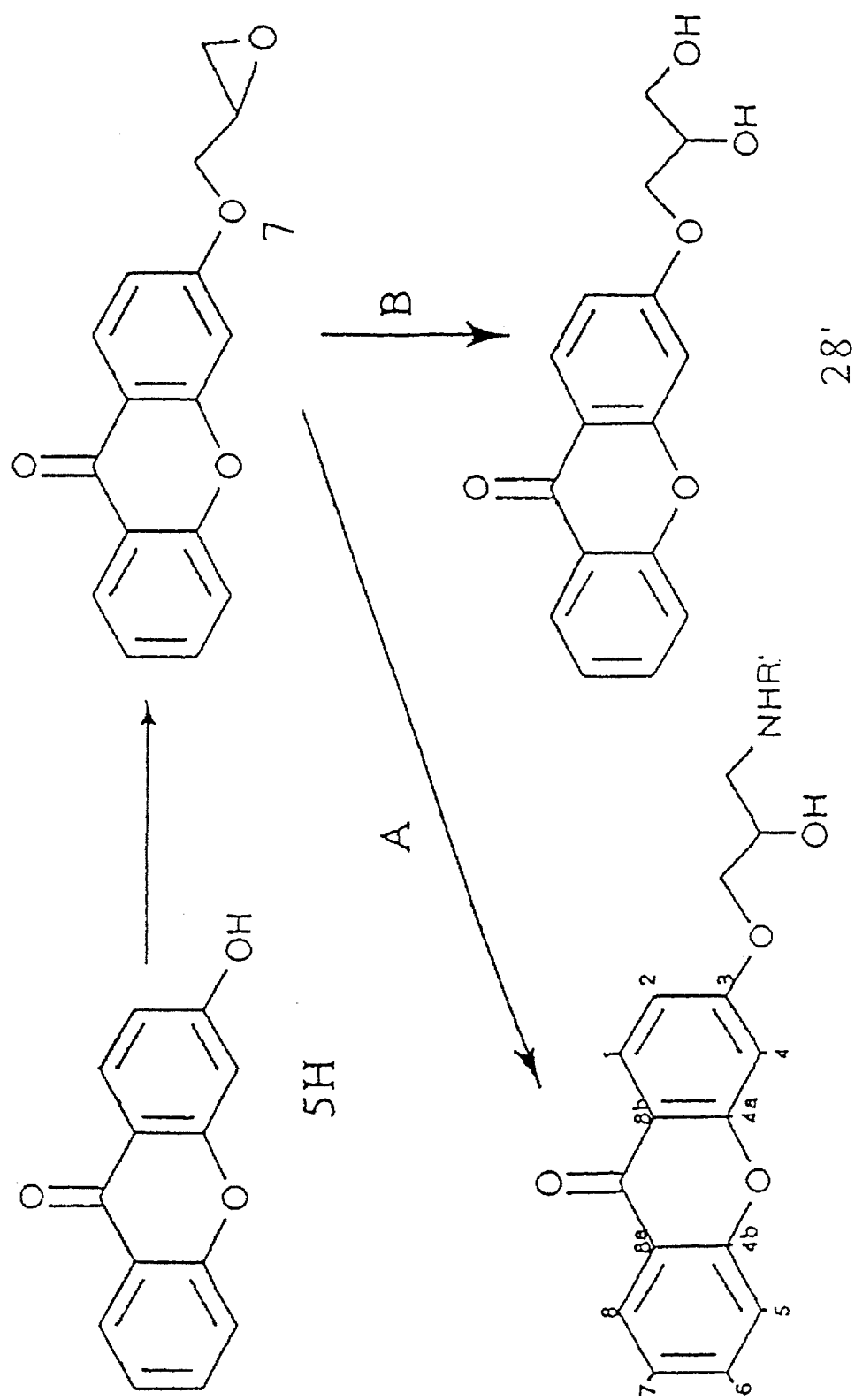

Although some active xanthone derivatives can be isolated from natural sources, the production is not economical due to their limited yield and the time-consuming procedures. As shown in FIG. 2, various benzenes were used to synthesize benzophenone precursors, and then cyclization was carried out to yield monooxygenated, dioxygenated and tetraoxgenated xanthones. Various derivatives of xanthone epoxides can be produced (as shown in FIG. 3) by reacting 3-hydroxyxanthone (5H) in isopropanol aqueous solution of NaOH (in appropriate amount) with epichlorohydrin (in excess amount). 3-(2,3-epoxypropoxy)-xanthone (7) as the main product. Based on route A, 3-( 2,3-epoxypropoxy )-xanthone ( 7 ) with various amines (in appropriate amount) can be refluxed in absolute alcohol to yield various xanthonoxypropanolamines. Based on route B, 3-(2,3-epoxypropoxy)-xanthone (7) reacted with 10 % NaOH aqueous solution (in appropriate amount) in isopropanol and yielded 3-(2,3-dihydroxypropoxy)-xanthone (28'). The purified compounds were identified by UV, IR. $^1$H-NMR, $^{13}$C-NMR, EIMS and physical properties.

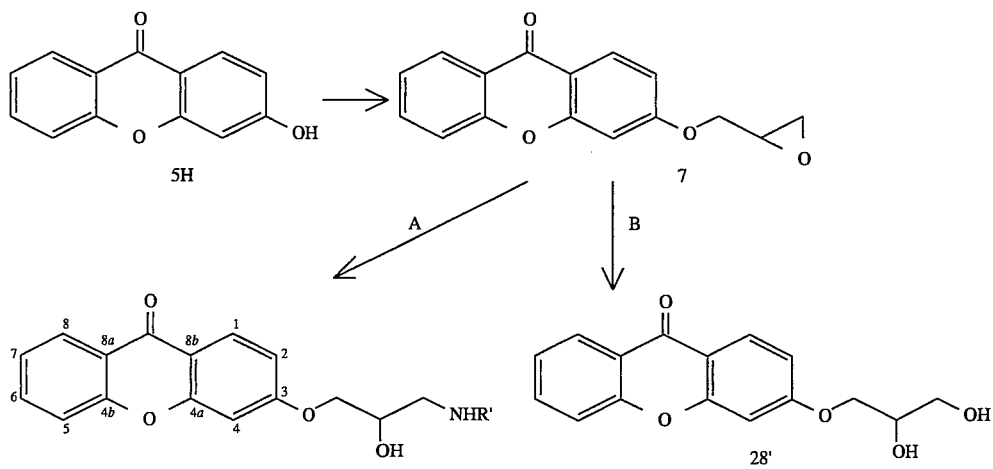

Figure 3.

The synthesized compounds in this invention include xanthones (shown as formula I) and benzophenones (shown as formula II). There are a total of 7 substituents on a xanthone derivative. They can be hydrogen, hydroxy group, $C_{1-6}$ alkyl (oxy) group, or $C_{1-12}$ alkyl propanolamine. At the most, six of the substituents can simultaneously be hydrogen, methoxy group, or hydroxy group. The substituent, hydroxy group can be converted to acetyl ester. One of the substituents can be propanolamine with $C_{1-12}$ alkyl group; that is a structure of ORNHR' where R is a secondary propanol and R' is a $C_{1-8}$ alkyl group such as hexane with methyl substituent or acyclic alkanes. There are 9 substituents on a benzophenone and six of them, at the most, can be methoxy or hydroxy group at the same time.

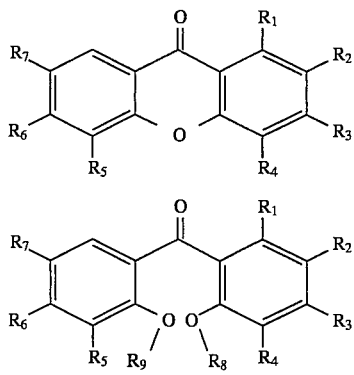

It is known that ADP, arachidonic acid, PAF and collagen treatment will lead to the aggregation of rabbit platelet. As for the correlation between the structure and biological functions of xanthone derivatives, it was found that xanthones with oxygenated group on C-3 are an important moiety to cause platelet aggregation. Using 10 μg/ml of collagen as inducer of platelet aggregation, tile replacement of the methoxy or hydroxy group on the C-3 by the 3-propylamino-2-hydroxypropoxyl group increases the inhibitory effect on platelet aggregation. The reaction mechanisms of 1,3,6,7,-tetraoxygenated xanthones and 3,4-dihydroxygenated xanthone inhibit the formation of $A_2$-thromboxane and the degradation of phosphoinositide, and inhibit the activity of $A_2$-thromboxane, respectively. In addition, xanthones with γ-pyrone structure like flavonoxypropanolamines showed anti-hypertensive activity. In this invention, a series of xanthone derivatives were examined to elucidate the correlation between structure and biological activities, and they were found to have antithrombotic or/and antihypertensive activities. Furthermore, we synthesized various xanthonoxypropanolamines and related compounds and experimentally showed their activity inhibiting platelet aggregation as indicated in FIG. 4–6 and Table 1-3.

Figure 4:
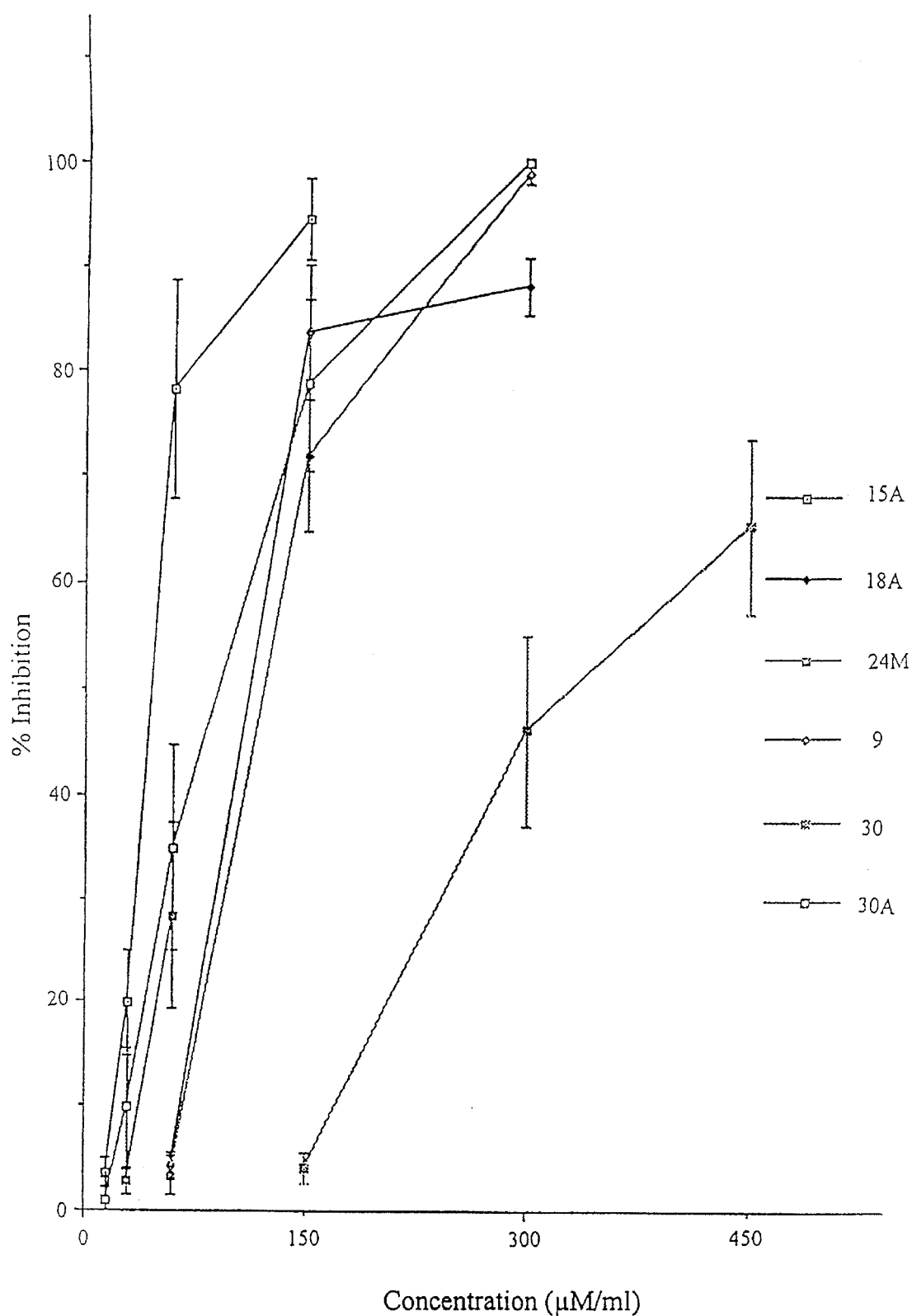
Figure 5:
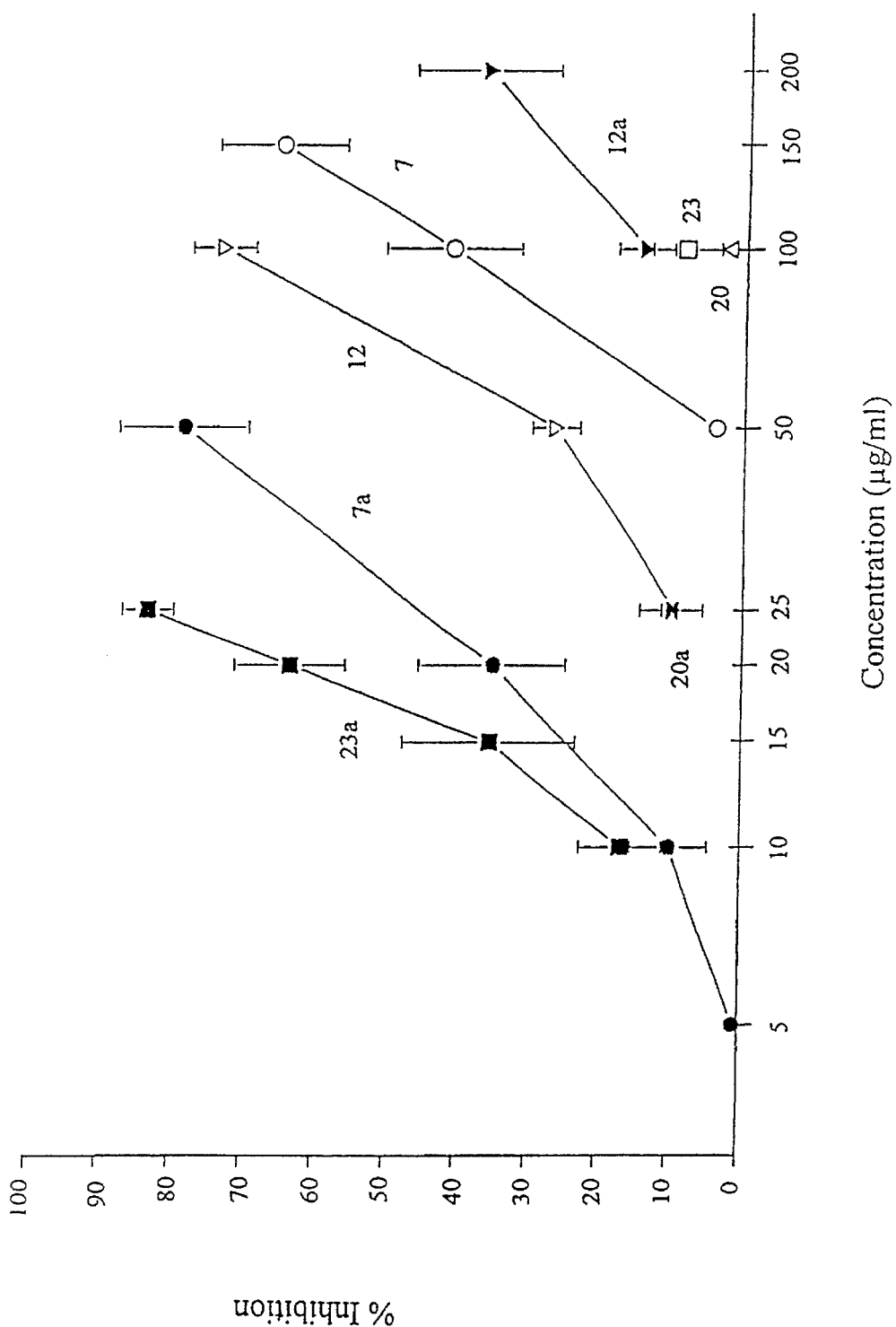
Figure 6:
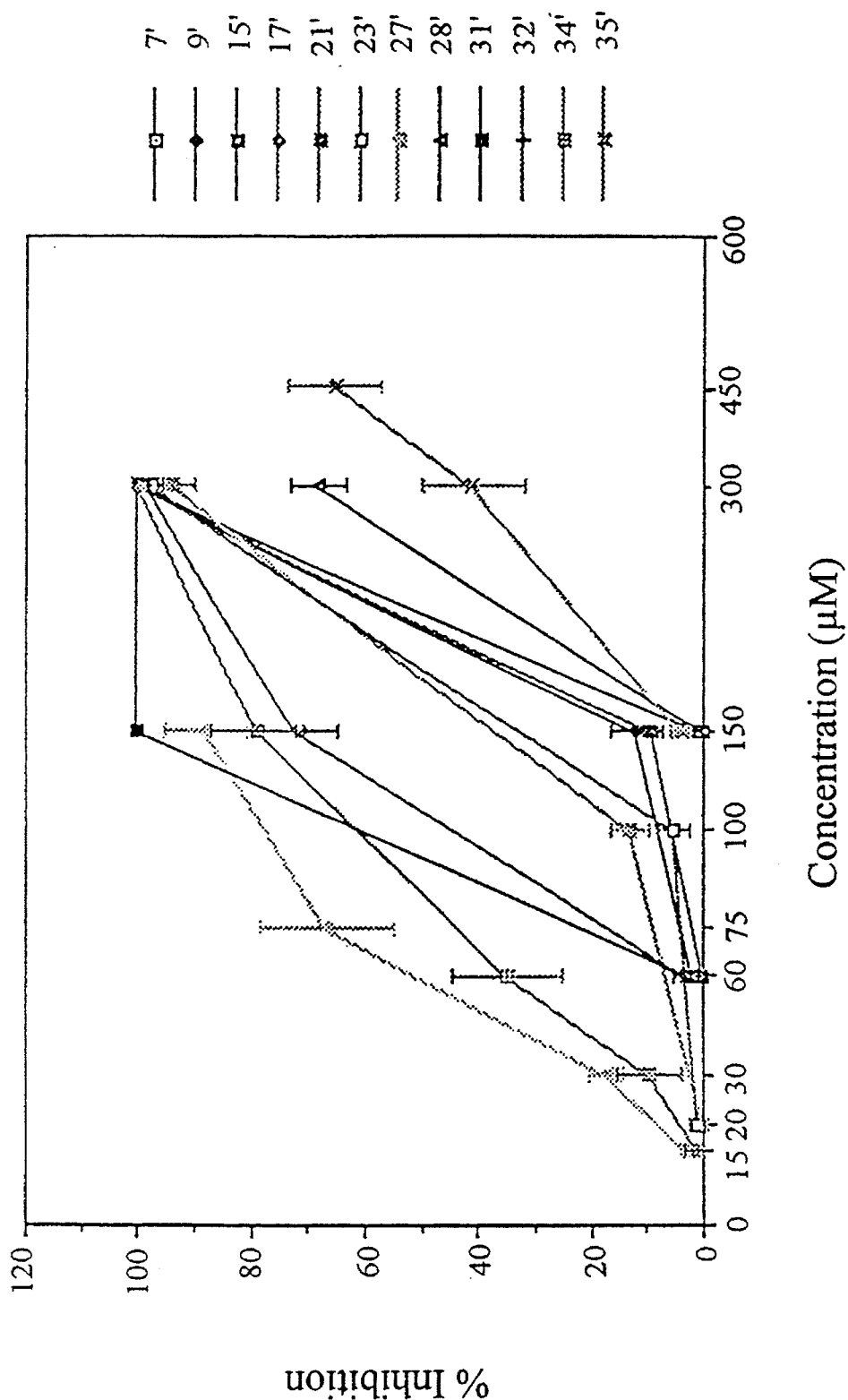

Among the synthesized derivatives, 2,3-dihydroxyxanthone diacetate, 3,4,6,7-tetrahydroxyxanthone tetraacetate and 3-(3-cyclohexylamino-2-hydroxypropoxy) xanthone had more significant effect on inhibiting collagen-induced platelet aggregation than norathyrol, as shown in FIG. 4–6, Table 1-3. Among them, 2,3-dihydroxyxanthone at a dose of 100 μg/ml could significantly inhibit both the muscle contraction in rat's thoracic aorta (which was induced by 1.9 mM calcium ion at high potassium ion concentration of 80 mM) and the phasic or tonic muscle contraction (which was induced by 3 mM norepinephrine). 2,3-Dihydroxyxanthone also significantly lowered the blood pressure of anesthetized rats. In addition to its effect on reducing the blood pressure of anesthetized rats, 3,4,6,7-tetrahydroxyxanthone had strong inhibitory activity toward the angiotension I converting enzyme and achieved a $IC_{50}$ of 35.38 μM.

Among the xanthonoxypropanolamines sythesized in this invention, 3-(3-propylamino-2-hydroxypropoxy) xanthone and 3-(3-Isopropylamino-2-hydroxypropoxy) xanthone could significantly reduce the blood pressure and slow down the heart beat of the anesthetized rat as shown in FIG. 8–11. 3-(3-Isopropylamino-2-hydroxypropoxy) xanthone at a concentration of $10^{-4}$ M could significantly inhibit the contraction of rat's thoracic aorta induced by high potassium ion concentration of 100 mM.

Based on the method of Teng et. al. (Ouyang, C. Biochem. Biophys. Acta. 1987, 924:375), rabbit platelets were washed with platelet-rich plasma which was adjusted with EDTA for anti-aggregation. Counted by Coulter Counter (model, ZM), the platelets were adjusted to a density of $4.5 \times 10^8$ platelets/ml by Tyrode's solution which contains 136.8 mM NaCl, 2.8 mM KCl, 1.0 mM $CaCl_2$ and 11.2 mM glucose, and 0.35% bovine serum albumin. Platelets were agitated at a speed of 1200 rpm to form a suspension. All xanthone derivatives tested were dissolved in DMSO. The concentration of DMSO was limited to 0.5% to prevent its interference to the aggregation reaction. The aggregation was assayed by O'Brin's turbidometer. To determine the degree of aggregation, the absorbance of platelet suspension was referred as 0% aggregation and that of the platelet without Tyrode's solution was used for 100%. Lumiaggregometer (Chromo-Log Co. USA) was used to carry out the aggregation assay.

The compounds of this invention can be manufactured into tablets or other solid-form pharmaceuticals by adding various excipients such as magnesium stearate, lactose, and starch. On the other hand, pH adjustment by phosphate buffer would be suitable for the production of liquid type drugs for injection or other purpose. Compounds of formula I and II in this invention can be prepared to salts by adding acid; pharmacologically, the pharmaceuticals made from these salts can achieve the antithrombotic and antihypertensive effects. The exact dose and regime for administration of these compounds will depend on the symptoms and the requirement of the patients. For an adult, dosage between 50 to 300 mg, three times per day is usually preferred.

EXAMPLE 1

2-Hydroxy-4-methoxy-2'-methoxybenzophenone, 4a 2,4-dimethoxy-2'-hydroxybenzophenone, 4b To a solution 2.0 g (13.14 mmol) of 2-methoxybenzoic acid in 60 ml of dry benzene, 5 ml oxalyl chloride was added under stirring at room temperature. After 2 hours, solvent and excess reagents were removed at reduced pressure. The residual 2-methoxybenzoyl chloride was dissolved in 80 ml of anhydrous ether, and then 1.8 g (13.03 mmol) of 1,3-dimethoxybenzene and 5.0 g of aluminum chloride were added. After stirred at room temperature for 8 hours, the resulting mixture was hydrolyzed by 500 ml of ice water containing 45 ml of concentrated HCl and then extracted with chloroform. The solvent was removed to give a crude product. After purified by column chromatography, 2.20 g (8.53 mmol) of a yellow oily product was obtained and the yield was 65%. The data of the physical properties of the compounds were measured and are listed below.

$^1$H NMR(CDCl$_3$): δ3.76, 3.82 (2s, 12H), 6.33 (dd, J=8.5, 2.4Hz, 2H), 6.47 (d, J=2.4Hz, 2H), 7.01 (m, 4H, aromatic H), 7.24 (m, 4H, aromatic H), 7.42 (m, 2H, aromatic H), 12.72 (s, 2H).

EXAMPLE 2

3-Methoxyxanthone, 5M 2.20 g (8.53 mmol) of 2-hydroxy-4-methoxy-2'-methoxybenzophenone (4a), and 2,4-dimethoxy-2'-hydroxybenzophenone (4b) were added to a solution of pyridine (100ml), water (50ml), and 10% aqueous tetramethylammonium hydroxide. After being heated and refluxed for 36 hours, the mixture was poured into ice and subsequently acidified with HCl. The resulting mixture was extracted with ether and an oily product was generated. After purified by column chromatography on silica gel and crystallized from CHCl$_3$, 1.6 (7.08mmol) of 3-methoxyxanthone (5M) as colorless powder were obtained. The yield was 83%. The physical properties were measured and are shown below.

mp: 116°–117° C. MS (m/z, %): 226 (100) (M$^+$); IR ($^v$max, KBr): 1650 cm$^{-1}$ $^1$H-NMR(CDCl$_3$): see Table 5 Elementary Analysis: (C$_{14}$H$_{10}$O$_3$) C, H.

EXAMPLE 3

3-Hydroxyxanthone, 5H 1.6g (7.08mmol) of methoxyxanthone was refluxed at 160° C. in a mixture of hydrogen Iodide (35ml) and phenol (42ml) for 8 hours. The resulting mixture was then poured into NaHSO$_3$ aqueous solution and it generated a yellow precipitate. The precipitate was collected and purified with silica gel column chromatography (eluted with chloroform-methanol 4:1). 1.40g (6.60 mmol) of 3-hydroxyxanthone (5H), a yellow needles, were crystallized from methanol and the yield was 93%. The data of the physical properties are listed below.

mp :241°–242° C.; MS (m/z, %) :212 (100) (M$^+$); UV: λmax (MeOH) nm (log ε) : 235 (4.06), 265 (3.39), 330 (3.59); λmax (MeOH +NaOAc) : 230, 265 (sh), 335; IR (KBr) : 3115, 1615 cm$^{-1}$ $^1$H-NMR (DMSO): see Table 5 Anal. (C$^{13}$H$_8$O$_3$) C, H.

EXAMPLE 4

3-Hydroxyxanthone acetate, 5A

To a solution of 0.2g (0.94 mmol) of 3-hydroxyxanthone (5H), dissolved in 10ml of dry pyridine, was added 10ml of anhydrous acetic anhydride. The resulting mixture was reacted for 4 hours. After purified by flash column chromatography and recrystallized from MeOH, 0.22g (0.87 mmol) of 3-hydroxyxanthone acetate (5A), as colorless needles was obtained and the yield was 92%. The data for its physical properties were listed below.

mp : 148°–149 ° C.; MS (m/z) %: 254(30) (M$_+$), 212 (100); IR (KBr) : 1755, 1665, 1610 cm$^{-1}$; $^1$H-NMR(CDCl$_3$): see Table 5; $^{13}$C-NMR(CDCl$_3$): see Table 6; Elementary Analysis: (C$_{15}$H$_{10}$O$_4$) C, H.

EXAMPLE 5

3-(2,3-Epoxypropoxy) xanthone, 7

To a solution of 0.19g (4.71 mmol) of sodium hydroxide in 6.18ml of isopropanol and 1.3ml of water, 1.00g (4.72 mmol) of 3-hydroxyxanthone (5H) and 3.76ml (46.86 mmol) of epichlorohydrin were added. The components were reacted under stirring at 70° C. for 2 hours. The resulting mixture was filtered to remove side product (dimer). The filtrate was concentrated in reduced pressure at 50~60° C. and 10ml of isopropanol was added to the resultant residue. The mixture was refluxed and was then filtered to remove the dimer. The clear filtrate was allowed to cool, and the generating solid was then washed with 1.40 ml of isopropanol and dried in air to give 945 mg (4.46 mmol) of brown product. The yield was 74%. Purified by chromatography on silica gel and crystallized from dichloromethane, colorless powder of 3-(2,3-epoxypropoxy) xanthone (7) was obtained. The measured date of physical properties are listed below.

mp : 157°–158° C. Ms (m/z) % : 268 (100) (M$^+$); IR (KBr) : 1645, 1265 cm$^{-1}$; $^1$H-NMR(CDCl$_3$): δ2.79–2.99 m, CH$_2$ of epoxy ring, 3.42 (m, 1H, CH of epoxy ring) 4.05 (dd, J=11, 6.0, 1H), 4.39 (dd, J=11, 3.0 Hz, 1H), 6.91 (d, J=2.4Hz, 1H, H-4), 6.95 (dd, J=9.0. 2.4Hz, 1H, H-2), 7.27–7.47 (m, 2H, H-6 and H-7), 7.65–7.70 (m, 1H, H-5), 8.26 (d, J=9.0Hz, 1H, 1-H), 8.32 (dd, J=9.0, 1.5Hz, 1H, H-8); $^{13}$C-NMR(CDCl$_3$): δ44.5 CH$_2$ of epoxy ring), 69.2 (OCH$_2$) 49.7 CH of epoxy ring, 101.1 (C-4), 113.4 (C-2), 116.2 (C-8b), 117.7 C-5), 121.9 (C-8a), 123.9 (C-7), 126.6 (C-8), 128.4 (C-1), 134.3 (C-6), 156.2 (C-4b), 157.9 (C-4a), 163.7 (C-3), 176.2 (CO); Anal. (C$_{16}$H$_{12}$O$_4$);

EXAMPLE 6

3 [3-(propylamino)-2-hydroxypropoxy]xanthone (9)

900 mg (3.36 mmol) of 3-(2,3-epoxypropoxy)xanthone (7) and 20 ml of absolute ethanol were added to 20.0 ml (244 mmol) of n-propylamine. The mixture was heated under stirring. After the reaction, the mixture was filtered and the filtrate was concentrated in reduced pressure. It was then refiltered and washed with absolute ethanol. After purified by chromatography on silica gel (eluent with chloroform-methanol 4:1), 0.6 g (1.85 mmol), 3[3-(propylamino)-2-hydroxypropoxy]xanthone (9), recrystallized from chloroform as pale yellow powder. The yield was 55%. The physical properties of the compound were determined and are listed below.

mp: 109°–110° C.; MS (m/z) %:

328 (3), (M$^{+1}$), 327(M$^+$), 298 (10), 283 (19), 212 (44), 72 (100); IR (KBr) : 3525, 3275, 1670, 1660 cm$^{-1}$; $^1$H-NMR (CDCl$_3$) : δ0.95 (t, J=7.2 Hz, 3H), 1.55 (qt, J=7.2 Hz, 2H), 2.64 (dt, J=12, 7.2 Hz, 1H), 2.65 (dt, J=12.2, 7.2 Hz, 1H), 2.78 (dd, J=12.2, 7.2 Hz, 1H), 2.90 (dd, J=12.2, 3.5 Hz, 1H), 4.11 (s,3H), 6.90 (d, J=2.2 Hz, 1H), 6.95 (dd, J=9.0, 2.2 Hz, H-2), 7.32–7.46 (m, 2H, H-6 and H-7), 7.70 (m, 1H, H-5), 8.24 (d, J=9.0 Hz, H-1) 8.31 (dd, J=9.0, 2.2 Hz, 1H, H-8); $^{13}$C-NMR (CDCl$_3$): δ11.7 (CH$_3$), 23.2,(CH$_2$CH$_3$), 51.5 (CH$_2$CHOH), 51.7 (CH$_2$CH$_2$NH), 67.9 (OCH$_2$), 71.1 (CHOH), 100.9 (C-4), 113.5 (C-2), 115.9 (C-8b), 117.7 (C-5),121.9 (C-8a), 123.9 (C-7), 126.6 (C-8),128.3 (C-1), 134.3 (C-6), 156.2 (C-4b), 157.9 (C-4a),164.1 (C-3), 176.3 (CO); Anal.(C$_{19}$H$_{21}$O$_4$N. H$_2$O) C, N, H.

EXAMPLE 7

4, 6-Dimethoxy-2-hydroxy-2'-methoxybenzophenone, 11a

2, 4, 6-Trimethoxy-2'-hydroxybenzophenone, 11 b

Based on the method to produce 2-hydroxy-4-methoxy-2'-methoxybenzophenone (4a) and 2,4-dimethoxy-2'-hydroxybenzophenone (4b), 2.0 g (13.14 mmol) of 2-methoxybenzoic acid was reacted with 2.19 g (13.04 mmol) of 1,3,5-trimethoxy benzene to give 2.20 g (7.75 mmol) of pale yellow powder. The yield was 59%. The physical properties of the compound obtained were determined and are listed below.

$^1$H-NMR, CDCl3: δ3.64, 3.67, 3.77, 3.81 (4s, 18H, 6OMe), 5.81 (d, J=2.4 Hz, 2H, H-5), 6.0( (d, J=2.4 Hz, 2H, H-3), 6.36–6.72 (m, 8H, H-3'—H-6'), 13.48(s, 2H, 2OH of 11a and 11b).

EXAMPLE 8

1, 3-Dimethoxyxanthone, 12M

Based on the method of producing 3-methoxyxanthone (5M), 2.20 g (7.75 mmol) of 4 6-dimethoxy-2-hydroxy-2'-methoxybenzophenone (11a) and 2,4,6-trimethoxy-2'-hydroxyphenone (11b) were reacted to give 1.65g (6.45 mmol) of 1,3-dimethoxyxanthone (12M) as colorless powder. The yield was 83%. The physical properties of the compound were measured and are listed below.

mp: 170°–171° C.; MS (m/z) %: 256 (100) (M$^+$); IR (KBr): 1660 cm$^{-1}$; $^1$H-NMR (CDCl$_3$): see table (5); Anal. (C$_{15}$H$_{12}$O$_4$. ⅓H$_2$O) C, H.

EXAMPLE 9

3,4-Dihydroxyxanthone, 18H

According to the method of producing 2-hydroxy-4-methoxy-2'-methoxy benzophenone (4a) and 2,4-dimethoxy-2'-hydroxybenzophenone (4b), 2.00g (13.14 mmol) of 2-methoxybenzoic acid was reacted with 2.19g (13.04 mmol) of 1,3,5-trimethoxybenzene to give 2.20g (7.75 mmol) of 3,4-dimethoxy-2-hydroxy-2'-methoxybenzophenone (17a) and 2,3,4-trimethoxy-2'-hydroxy-benzophenone (17b). Then, based on example 3, 1.35 g (5.92 mmol) of 3,4-dihydroxy benzophenone (18H) as pale yellow powder was produced. The physical properties were measured and are listed below.

mp: 238°–240° C.; MS (m/z) %: 228 (100) (M$^+$) UV: λmax (MeOH) nm, (logε): 207 (3.80), 237 (4.18), 255 (4.08), 285 (sh) (3.49), 315 (3.74); λmax (MeOH+NaOAc) : 205, 235, 255 (sh), 288 (sh), 320; λmax (MeOH+NaOAc+ H3BO3): 208, 235, 265, 285(sh), 320. IR (KBr): 3200, 1640 cm$^{-1}$; $^1$H-NMR (CDCl$_3$) : see table 5 Anal.(C$_{13}$H$_8$O$_4$) C, H.

Based on the examples described above, the following compounds can be produced.

Formula 1

For the compounds in the examples shown below, the R of unlabelled substituents are all hydrogen (H)

| example | compounds | |
|---|---|---|
| 10 | 1,3-Dihydroxyxanthone (12H) | R$_1$ = R$_3$ = OH |
| 11 | 1,3-Dihydroxyxanthone diacetate (12A) | R$_1$ = R$_3$ = OAc |
| 12 | 2,3-Dimethoxyxanthone (15M) | R$_2$ = R$_3$ = OCH$_3$ |
| 13 | 2,3-Dihydroxyxanthone (15H) | R$_2$ = R$_3$ = OH |
| 14 | 2,3-Dihydroxyxanthone diacetate (15A) | R$_2$ = R$_3$ = OAc |
| 15 | 3,4-Dimethoxyxanthone (18M) | R$_3$ = R$_4$ = OCH$_3$ |
| 16 | 3,4-Dihydroxyxanthone diacetate (18A) | R$_3$ = R$_4$ = OAc |
| 17 | 3,5-Dimethoxyxanthone (21M) | R$_3$ = R$_5$ = OCH$_3$ |
| 18 | 3,5-Dihydroxyxanthone (21H) | R$_3$ = R$_5$ = OH |
| 19 | 3,5-Dihydroxyxanthone diacetate (21A) | R$_3$ = R$_5$ = OAc |
| 20 | 1,6-Dimethoxyxanthone (24M) | R$_1$ = R$_6$ = OCH$_3$ |
| 21 | 1,6-Dihydroxyxanthone (24H) | R$_1$ = R$_6$ = OH |
| 22 | 1,6-Dihydroxyxanthone diacetate (24A) | R$_1$ = R$_6$ = OAc |
| 23 | 2,6-Dimethoxyxanthone (27M) | R$_2$ = R$_6$ = OCH$_3$ |
| 24 | 2,6-Dihydroxyxanthone (27H) | R$_2$ = R$_6$ = OH |
| 25 | 2,6-Dihydroxyxanthone diacetate (27A) | R$_2$ = R$_6$ = OAc |
| 26 | 3,6-Dimethoxyxanthone (29M) | R$_3$ = R$_6$ = OCH$_3$ |
| 27 | 3,6-Dihydroxyxanthone (29H) | R$_3$ = R$_6$ = OH |
| 28 | 3,6-Dihydroxyxanthone diacetate (29A) | R$_3$ = R$_6$ = OAc |
| 29 | 3[3-(Isopropylamino)-2-hydroxypropoxyl)] xanthone (7') | |
| 30 | 3[3-(Cyclcopropylamino)-2-hydroxypropoxy] | |
| 31 | 3-[3-(1,1-Dimethyl-propylamino)-2-hydroxypropoxy] xanthone(25') | |
| 32 | 3-[3-(Cyclohexylamino)-2-hydroxypropoxy] xanthone (27') | |

-continued

| example | compounds | | 
|---|---|---|
| 33 | 3-(2,3-Dihydroxypropoxy) xanthone(28') | |
| 34 | 3,6,7-Trimethoxy-1-[3-(propylamino)-2-hydroxypropoxy] xanthone (31') | $R_3 = R_6 = R_7 = OCH_3$ |
| 35 | 3,4,6,7-Tetramethoxyxanthone | $R_3 = R_4 = R_6 = R_7 = OCH_3$ |
| 36 | 3,4,6,7-Tetrahydroxyxanthone (23") | $R_3 = R_4 = R_6 = R_7 = OH$ |
| 37 | 3'4'6'7'-Tetrahydroxyxanthone acetate (23" acetate) | $R_3 = R_4 = R_6 = R_7 = OAc$ |

Formula 2

| | |
|---|---|
| 38 | 4,6-Dimethoxy-2-hydroxy-2'-methoxybenzophenone (11a) |
| 39 | 2,4,6-trimethoxy-2'-hydroxy benzophenone (11b) |
| 40 | 4,5-Dimethoxy-2-hydroxy-2'-methoxybenzophenone (14a) |
| 41 | 2,4,5-trimethoxy-2'-hydroxy benzophenone (14b) |
| 42 | 3,4-Dimethoxy-2-hydroxy-2'-methoxybenzophenone (17a) |
| 43 | 2,3,4-trimethoxy-2'-hydroxy benzophenone (17b) |
| 44 | 2-hydroxy-4-methoxy-2',3'-dimethoxybenzophenone (20a) |
| 45 | 2.4-dimethoxy-2'-hydroxy-3'-methoxybenzophenone (20b) |
| 46 | 2-hydroxy-6-methoxy-2',4'-dimethoxybenzophenone (23a) |
| 47 | 2,6-dimethoxy-2'-hydroxy-4'-methoxybenzophenone (23b) |
| 48 | 2-hydroxy-5-methoxy-2',4'-dimethoxybenzophenone (26a) |
| 49 | 2,5-dimethoxy-2'-hydroxy-4'-methoxybenzophenone (26b) |
| 50 | 2-hydroxy-4-methoxy-2',4'-dimethoxybenzophenone (28a) |
| 51 | 2,4-dimethoxy-2'-hydroxy-4'-methoxybenzophenone (28b) |
| 52 | 3,4-dimethoxy-2-hydroxy-2',4',5'-trimethoxybenzophenone |
| 53 | 2,3,4-trimethoxy-2'-hydroxy-4',5'-dimethoxybenzophenone |

FIGURE LEGEND

Figure 7:
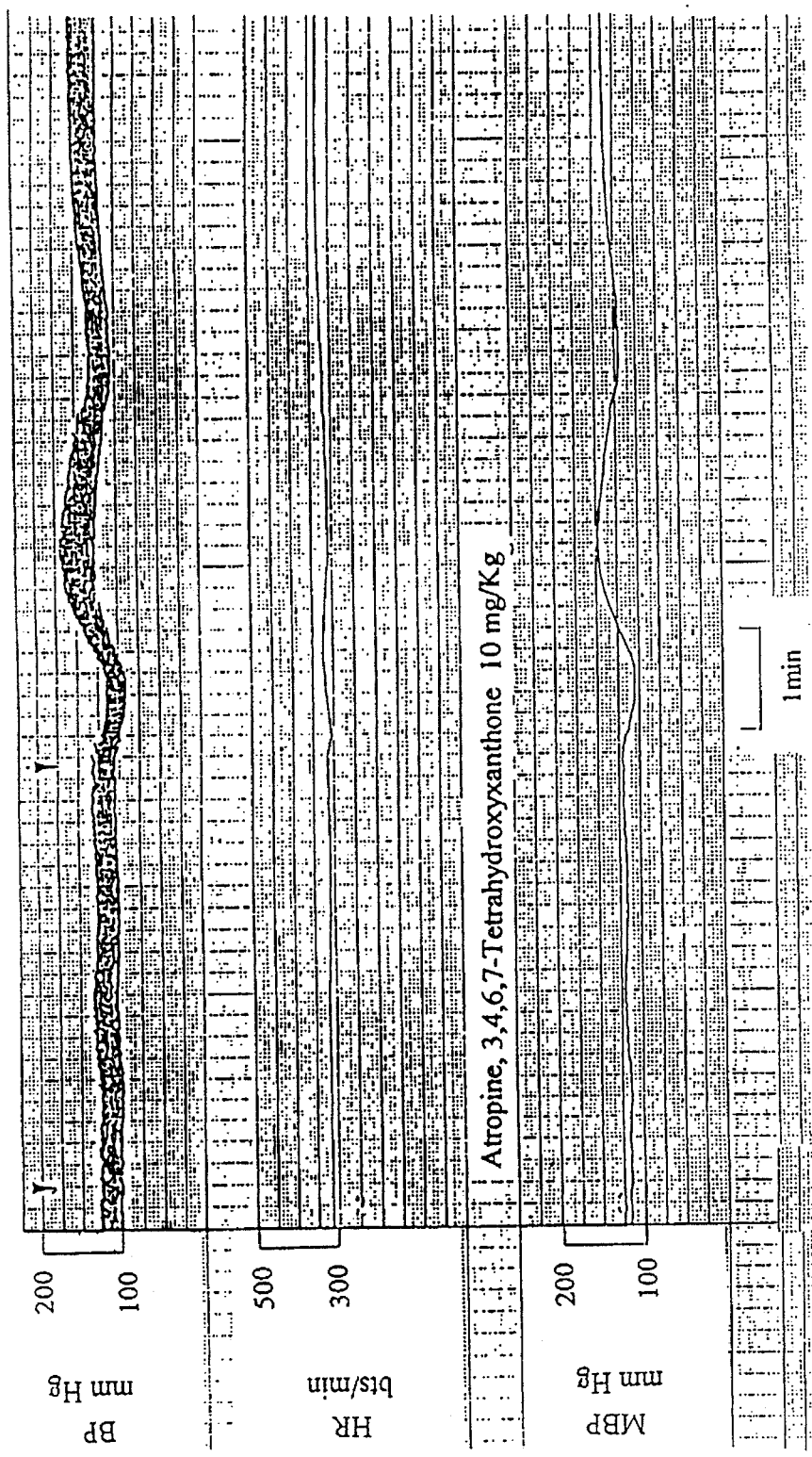
Figure 8:
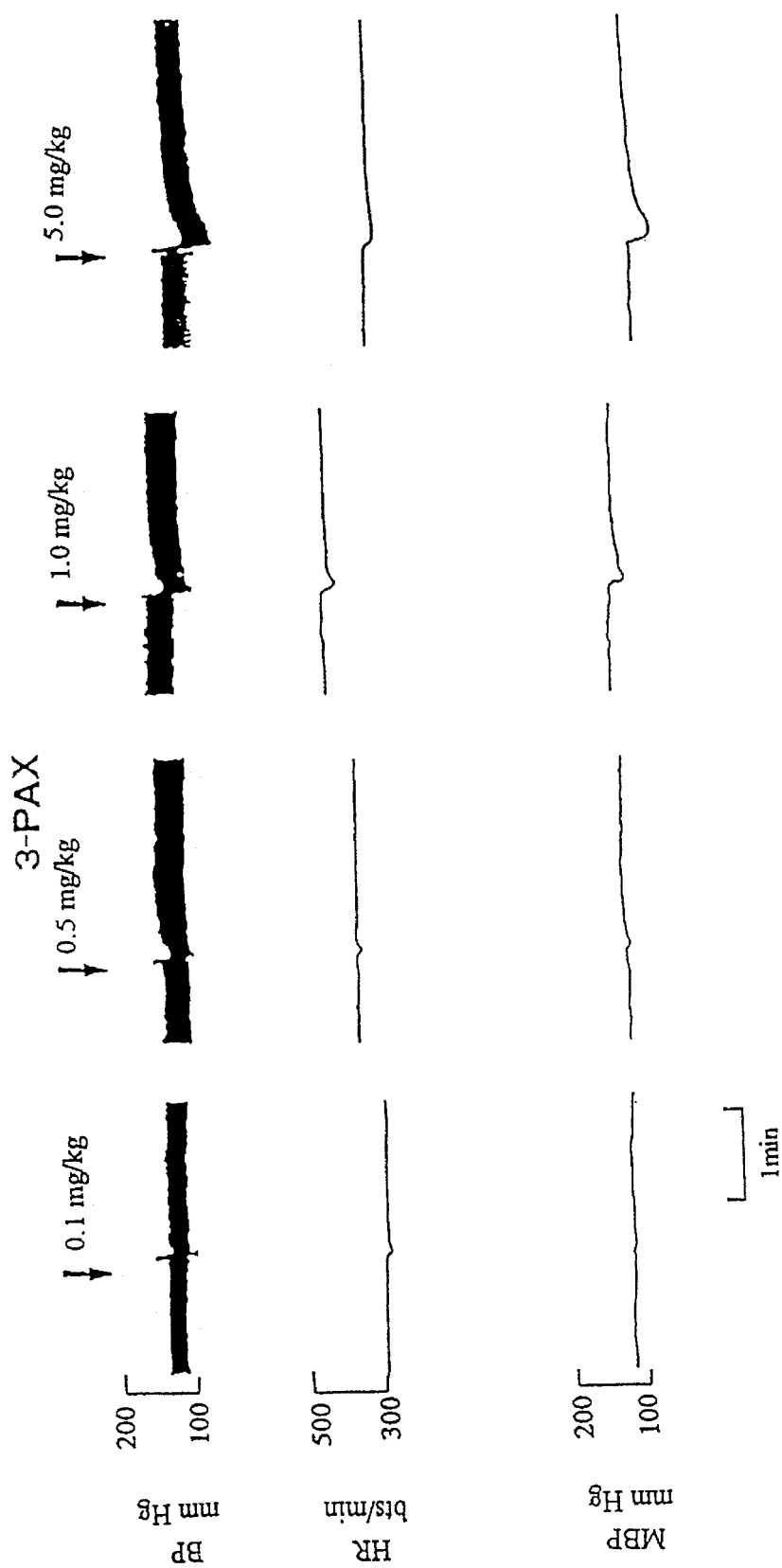
Figure 9:
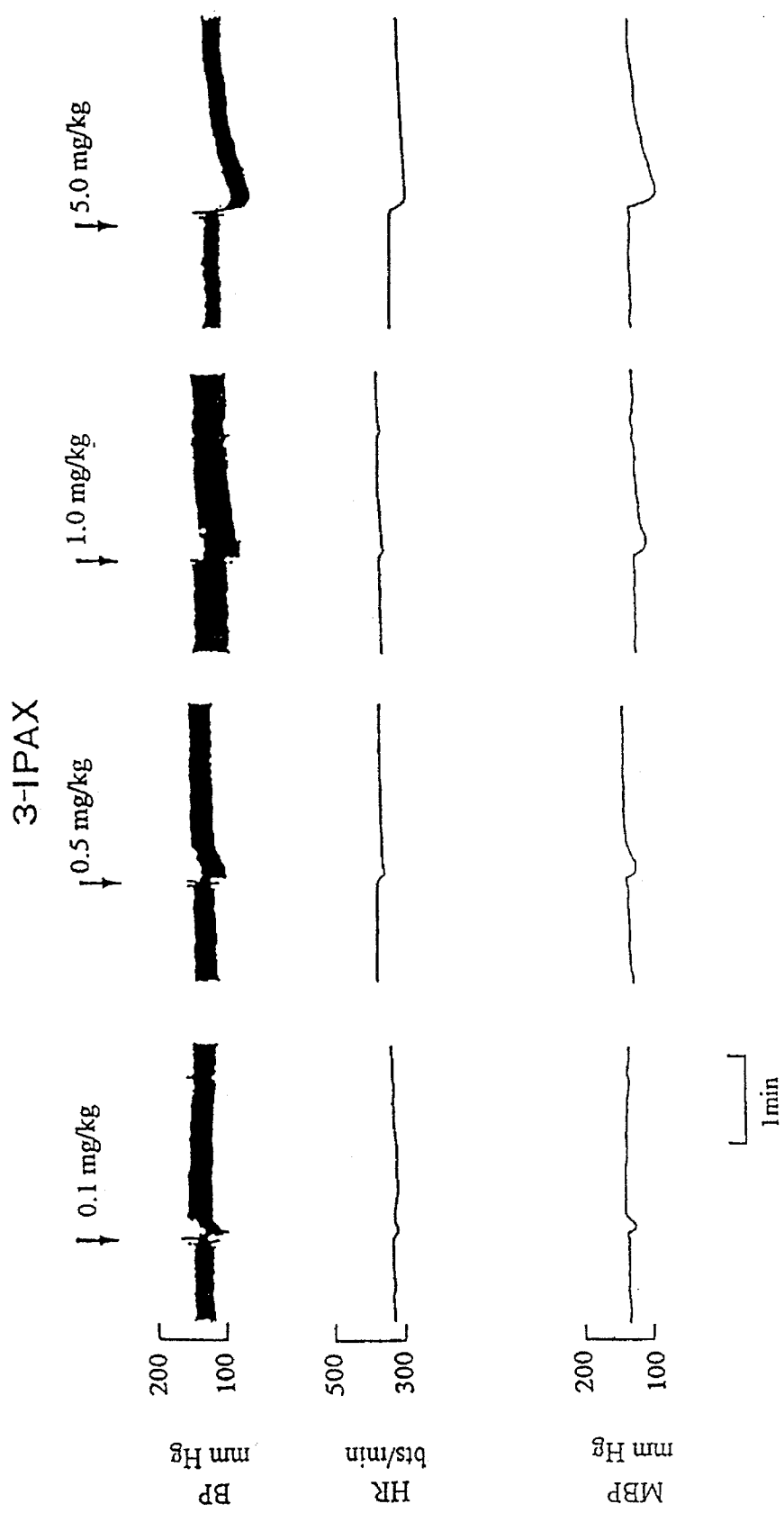
Figure 10:
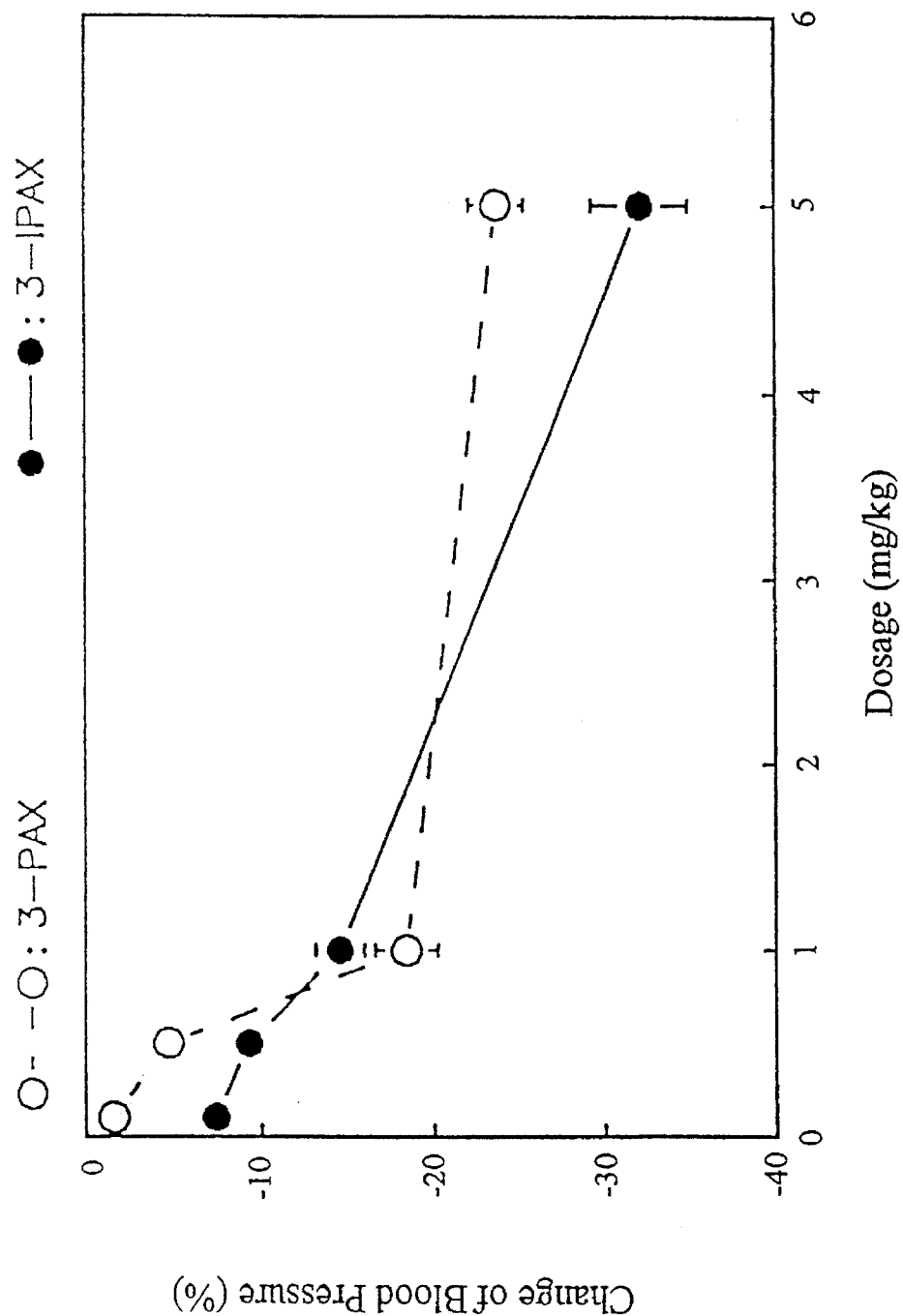
Figure 11:
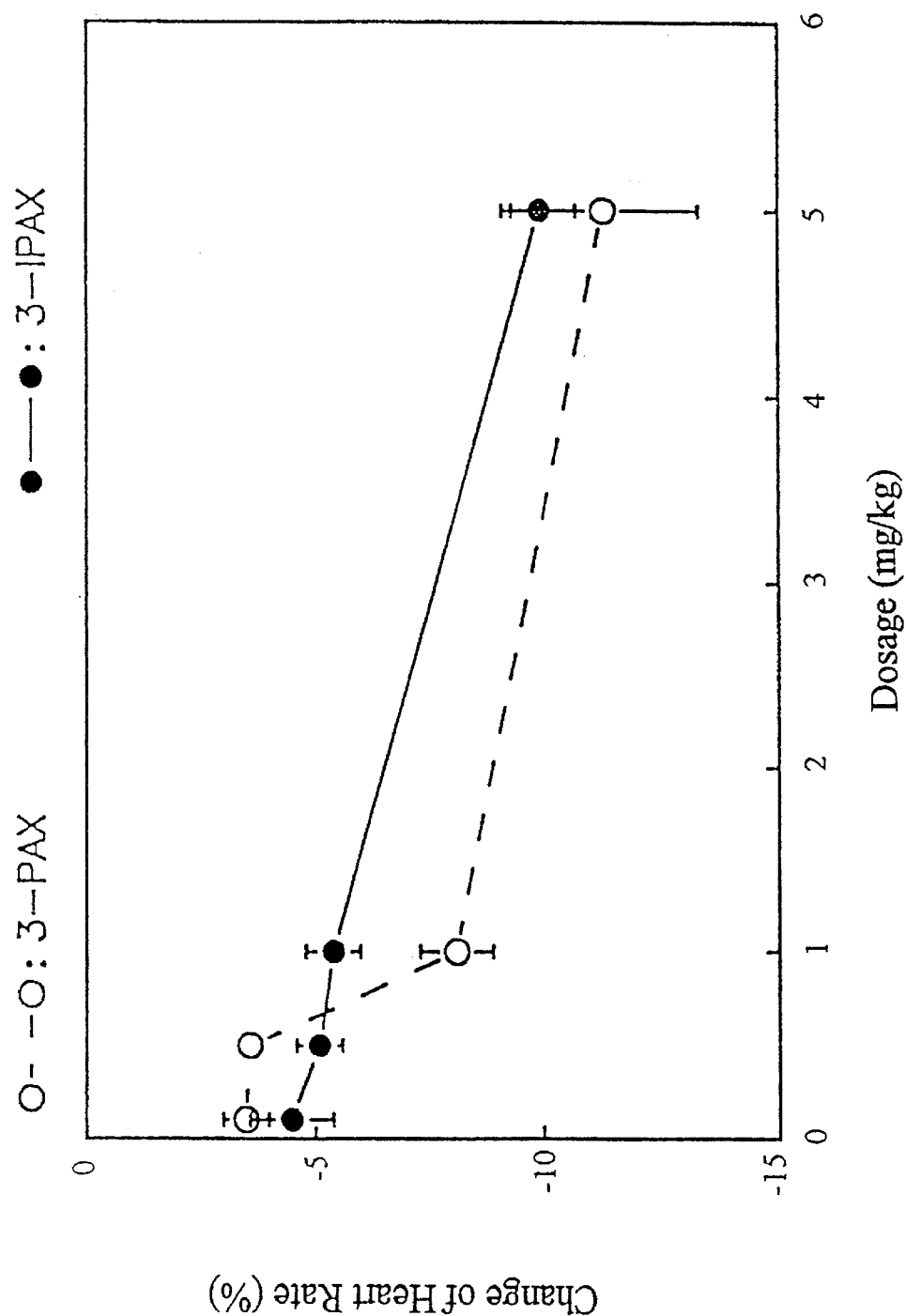
Figure 12:
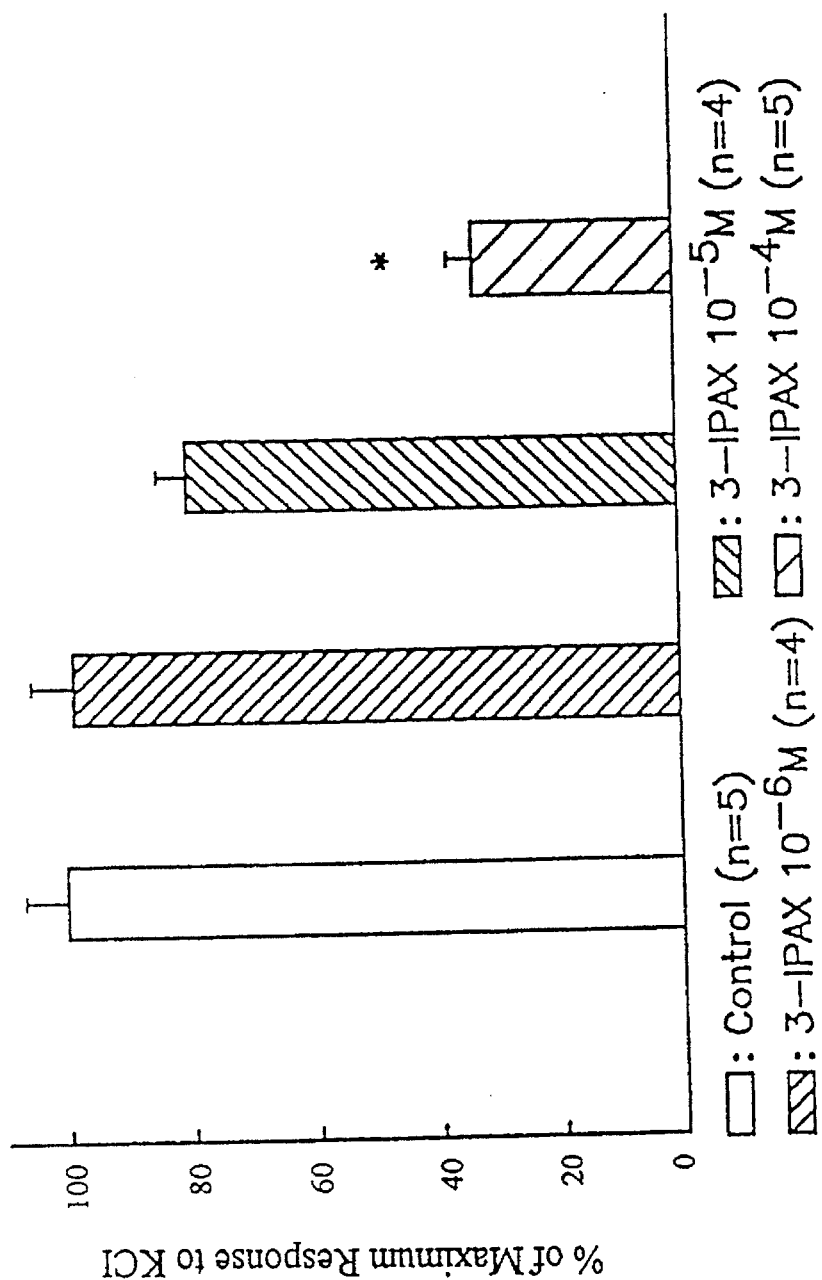

| | |
|---|---|
| Table 1 | The pharmacological activities of compound 5, 5H, 5A, 9, 12H, 12A, 15M, 15H, 15A, 18H, 18A, 21H, 21A, 24M, 24A, 27H, 27A, 29H, 19A. |
| Table 2 | The pharmacological activities of compound 3', 5', 7', 9', 11', 21', 23', 25', 27', 28', 29', 31', 32'. |
| Table 3 | The pharmacological activities of compound 12", 12" acetate, 16", 20", 20" acetate, 23", 23" acetate. |
| Table 5 | The $^1$H-NMR of compound 5M, 5H, 5A, 12M, 12H, 12A, 15H, 15A, 18M, 18H, 18A, 21M, 21H, 21A, 24M, 24H, 24A, 27M, 27H, 27A, 29M, 29H, 29A. |
| Table 6 | The $^{13}$C-NMR of compound 5A, 12A, 15M, 15H, 15A, 18M, 18H, 18A, 21M, 21H, 21A, 24M, 24H, 24A, 27H, 27A, 29M, 29H, 29A. |
| FIG. 4 | The inhibition for collagen-induced platelet aggregation of compound 9, 15A, 18A, 24M, 30, 30A. |
| FIG. 5 | The inhibition for collagen-induced platelet aggregation of compound 7", 7" acetate, 12", 12" acetate, 20", 20" acetate, 23", 23" acetate. |
| FIG. 6 | The inhibition for collagen-induced platelet aggregation of compound 7', 9', 15', 17', 21', 23', 27', 28', 31', 32', 34', 35'. |
| FIG. 7 | The typical record after atropine treatment: measuring the effect of 3,4,6,7-tetrahydroxyxanthone i.v. injection on blood pressure and heartbeat. |
| FIG. 8 | The examination of the effect of 3-[(3-propylamino)-2-hydroxy propoxy] xanthone (3-PAX) i.v. injection on blood pressure and heartbeat by typical record. |
| FIG. 9 | The examination of the effect of 3-[(3-isopropylamino)-2-hydroxy propoxy] xanthone (3-IPAX) i.v. injection on blood pressure and heartbeat by typical record. |
| FIG. 10 | The reaction curve showing the blood pressure as a function of the dosage of 3-PAX and 3-IPAX as i.v. injection. Each number was the average results from at least five measurements. |
| FIG. 11 | The reaction curve showing the heart beat as a function of the dosage of 3-PAX and 3-IPAX as i.v. injection. Each number is the average results from at least five measurements. |
| FIG. 12 | The constriction stress of rat's thoracic aorta induced by 100 mM KCl in the presence or absence of IPAX. The line represents the S.E. signal (P < 0.05) and the asterisk represents that the presence of 3-IPAX or not leads to significant variance. |

We claim:

1. A compound, and salts thereof, represented by the formula below:

wherein substituents $R_1$–$R_5$ and $R_7$ are, independently, hydrogen, hydroxy group, $C_{1-6}$ alkoxy group, acetyl ester or a $C_{1-12}$ alkyl-amino-2-hydroxy-propoxy group;

$R_6$ is either a hydroxy group or glucose;

at least three but no more than four of the substituents are alkoxy group, hydroxy group or acetyl ester;

at least one but no more than one of the substitutents is a $C_{1-12}$ alkyl-amino-2-hydroxy-propoxy group; and at least one of the $R_1$, $R_3$ or $R_7$ substituents is not a hydroxy group.

* * * * *